United States Patent [19]

Hesse

[11] Patent Number: Plant 6,834

[45] Date of Patent: Jun. 6, 1989

[54] CHRYSANTHEMUM PLANT NAMED WHITE DELIGHT

[75] Inventor: Peter S. Hesse, Bradenton, Fla.

[73] Assignee: Ball Seed Company, W. Chicago, Ill.

[21] Appl. No.: 150,062

[22] Filed: Jan. 29, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named White Delight having clear white daisy flowers with green immature disc florets; long peduncles, vigorous growth habit, strong stems, excellent flower keeping quality, and ideal suitability for use in year around cut flower programs.

1 Drawing Sheet

The present invention comprises a new and distinct cultivar of *Dendranthema grandiflora,* hereinafter referred to by the cultivar name White Delight.

White Delight is a product of a planned breeding program which had the objective of creating new Chrysanthemum cultivars with white daisy type flowers, long peduncles, green disc florets, and excellent keeping quality, these characteristics being ideally suited for year around cut flower programs. Such traits in combination were not present or needed improvement in previously available commercial cultivars.

White Delight was originated from a hybridization by applicant made in a controlled breeding program in Parrish, Fla. The female parent was an unknown seedling. The male parent of White Delight was Merriment, disclosed in U.S. Plant Pat. No. 5,285. White Delight was discovered and selected as one flowering plant within the progeny of the stated cross by applicant on Apr. 15, 1982 in a controlled environment in Parrish, Fla.

The first act of asexual reproduction of White Delight was accomplished when vegetative cuttings were taken from the initial selection in June 1982 in a controlled environment in Parrish, Fla. by a technician working under formulations established and supervised by applicant. Horticultural examination of selected units initiated in November 1982 has demonstrated that the combination of characteristics as herein disclosed for White Delight are firmly fixed and are retained through successive generations of asexual reproduction.

White Delight has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of White Delight, which in combination distinguish this Chrysanthemum as a new and distinct cultivar:

1. Clear white daisy flowers.
2. Green immature disc florets.
3. Produces little or no pollen.
4. Long peduncles, up to 30 cm with no growth regulator application.
5. Diameter across capitulum 7.5–9 cm.

6. Ray florets approximately 30–38 mm long and 8–12 mm wide.
7. Average of 28 ray florets per capitulum.
8. Most flower heads have one or two short, curly ray florets, as can be observed in the photographic drawing.
9. Vigorous growth habit, long peduncles and strong stems make it suitable for use as a cut flower year around.
10 Excellent flower keeping quality.

Of the many commercial cultivars known to the present inventor, the most similar in comparison to White Delight is the well known cultivar White Marble. In comparison to White Marble, White Delight has a one week earlier flower response, and no bract formation in the disc under stressful growing conditions. The white daisy flower type and excellent keeping qualities of White Delight are similar to those same characteristics of White Marble.

The accompanying photographic drawing shows typical inflorescence and foliage characteristics of White Delight, with colors being as nearly true as possible with illustrations of this type. The photograph is in black and white, with a few flowers being colored to accurately depict true flower color.

In the following description, color references are made to the Royal Horticultural Society Colour Chart. The color values were determined between 3:00 and 3:15 p.m. on Jan. 5, 1988 under fluorescent lighting at Parrish, Fla.

Classification:

*Botanical.*—*Dendranthema grandiflora,* cv. White Delight.

*Commercial.*—Cut daisy spray.

INFLORESCENCE

A. Capitulum:

*Form.*—Flat.

*Type.*—Single.

*Diameter across face.*—7.5–9 cm.

B. Corolla of ray florets:

*Color (general tonality from a distance of three meters).*—White.

*Color (upper surface).*—155D.

*Color (under surface).*—155D.

C. Corolla of disc florets:

*Color (mature).*—Yellow.

*Color (immature).*—143C.

D. Reproductive organs:

*Androecium.*—Present in disc florets only.

*Gynoecium.*—Present in both disc and ray florets.

PLANT

A. General appearance:

*Height.*—90 cm tall; height can vary depending upon growing conditions and cultural practices.

B. Foliage:

*Color (upper surface).*—147A.

*Color (lower surface).*—147B.

*Shape.*—Ovate, lobed and margins serrate.

I claim:

1. A new and distinct cultivar of Chrysanthemum plant named White Delight, as illustrated and described, and parts thereof.

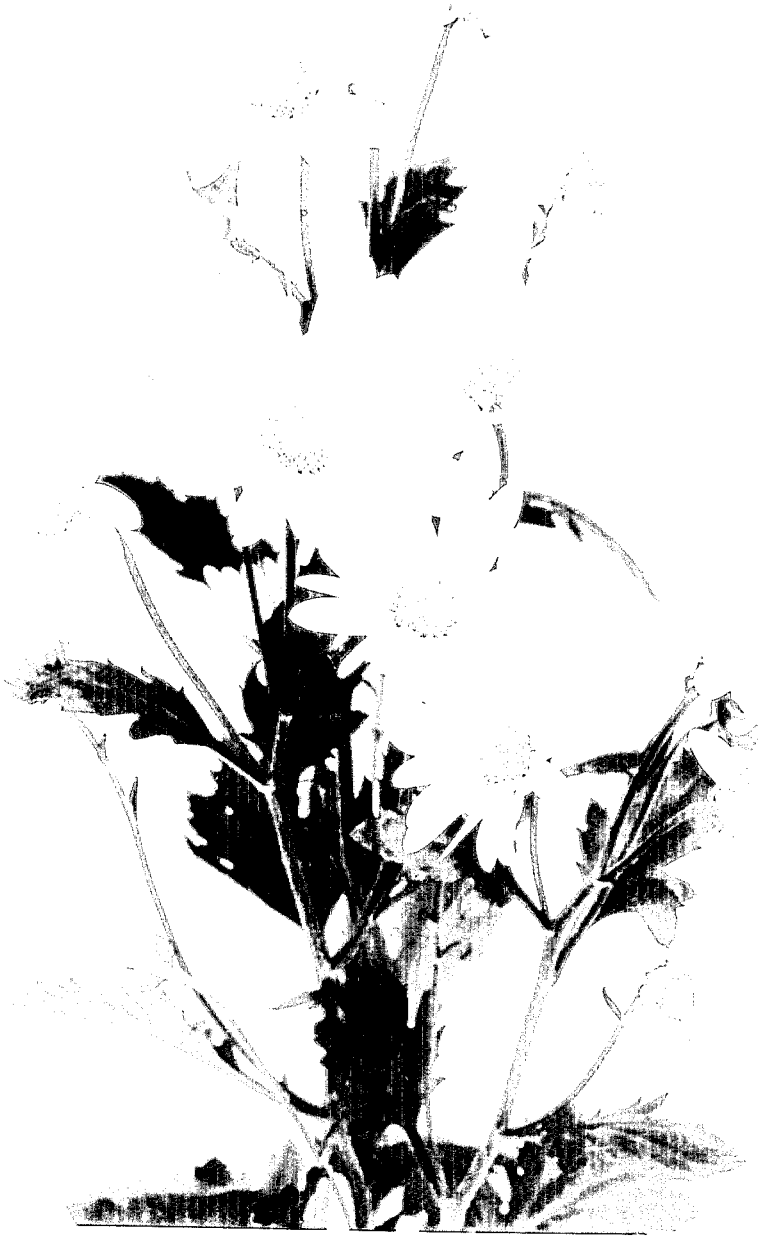

* * * * *